(12) United States Patent
Machan et al.

(10) Patent No.: US 8,693,628 B2
(45) Date of Patent: Apr. 8, 2014

(54) X-RAY SYSTEM

(76) Inventors: Lindsay S. Machan, Vancouver (CA); Daniel Gelbart, Vancouver (CA)

( * ) Notice: Subject to any disclaimer, the term of this patent is extended or adjusted under 35 U.S.C. 154(b) by 606 days.

(21) Appl. No.: 12/926,717

(22) Filed: Dec. 7, 2010

(65) Prior Publication Data

US 2011/0075805 A1 Mar. 31, 2011

Related U.S. Application Data

(63) Continuation-in-part of application No. 12/386,895, filed on Apr. 27, 2009, now Pat. No. 7,983,391.

(51) Int. Cl.
*G01N 23/04* (2006.01)
*H05G 1/64* (2006.01)
*G21K 1/04* (2006.01)

(52) U.S. Cl.
USPC ............................ 378/62; 378/98.2; 378/160

(58) Field of Classification Search
USPC ........................................... 378/62, 98.2, 95
See application file for complete search history.

(56) References Cited

U.S. PATENT DOCUMENTS

| | | | |
|---|---|---|---|
| 3,649,835 A | 3/1972 | Brackenbrough et al. | |
| 4,143,273 A | 3/1979 | Richey et al. | |
| 4,489,426 A | 12/1984 | Grass et al. | |
| 4,766,603 A | 8/1988 | Okabe et al. | |
| 4,868,843 A | 9/1989 | Nunan | |
| 4,928,297 A | 5/1990 | Tsutsui et al. | |
| 5,278,887 A | 1/1994 | Chiu et al. | |
| 5,422,926 A | 6/1995 | Smith et al. | |
| 5,568,533 A | 10/1996 | Kumazaki et al. | |
| 5,621,779 A | 4/1997 | Hughes et al. | |
| 6,320,936 B1 | 11/2001 | Holland et al. | |
| 6,792,078 B2 | 9/2004 | Kato et al. | |
| 7,315,610 B2 | 1/2008 | Freudenberger | |
| 2006/0067481 A1 | 3/2006 | Morton | |
| 2008/0118115 A1 | 5/2008 | Williamson | |

FOREIGN PATENT DOCUMENTS

JP 2005-095345 A 4/2005

*Primary Examiner* — Irakli Kiknadze
(74) *Attorney, Agent, or Firm* — Oyen Wiggs Green & Mutala LLP

(57) ABSTRACT

To reduce X-ray exposure while improving image quality, an area of interest is selected in the image. The image of the selected area is updated frequently, comparable to a rate of updates used today for the whole image. The rest of the image is updated at a significantly lower rate. Since the area of interest normally is a small part of the overall area, the total exposure is reduced significantly. A fast X-ray shutter, placed near the X-ray source, blocks the radiation from areas outside the area of interest. The shutter automatically retracts when the complete image is updated. The area of interest can be selected by the user or automatically selected based on activity in the image. Since most of the exposures are taken at a reduced collimation angle, limited by the area of interest, the area of interest is imaged at reduced scatter and better quality.

20 Claims, 7 Drawing Sheets

X-RAY SYSTEM

REFERENCE TO RELATED APPLICATIONS

This application is a continuation-in-part of U.S. patent application Ser. No. 12/386,895 filed 27 Apr. 2009 now issued as U.S. Pat. No. 7,983,391 and entitled SYSTEM FOR REDUCTION OF EXPOSURE TO X-RAY RADIATION which is hereby incorporated herein by reference for all purposes

FIELD OF THE INVENTION

The invention is in the medical field and in particular relates to real-time X-ray or fluoroscopy.

BACKGROUND OF THE INVENTION

The use of real-time, or continuous, X-ray is increasing rapidly because of the increased use of percutaneous medical procedures such as coronary stents, atrial ablation and gastric procedures. The doctors or other users in the operating room are forced to wear heavy lead aprons and sometimes goggles made of thick lead glass to avoid the cumulative effects of the X-ray radiation. A smaller dose of X-ray may reach persons far away from the X-ray machine. A common X-ray procedure is fluoroscopy, in which a portable arm carries an X-ray source at one end and a digital X-ray image sensor at the other end, with the patient placed between them. A screen connected to the image sensor via an image processing system displays real time images of the procedure. Some previous attempts to reduce the exposure of users to radiation used stationary lead shields, adjusted by the user. This is a time consuming operation. Other prior art solutions use electrically controlled masks that allow radiation to reach only part of the image. This is less than optimal, as without seeing the whole image it is difficult for the doctor to orient himself. The invention takes advantage of the fact that most of the image is changing very slowly and does not need as frequent updates as the area of interest. For example, when introducing a catheter into the body the area of interest is typically only around the catheter tip, but a much larger area needs to be seen for orientation. It is an object of the invention to reduce the X-ray exposure both for the patient and the doctor without degrading the image quality and information presented to the doctor. Another object of the invention is to improve image quality in the area of interest. A further object is to supply a system than can easily be incorporated into the design of existing fluoroscopy systems, or used as an add-on to existing systems. A further object is to introduce minimal changes in the use of the X-ray equipment compared to current practice, in order to avoid re-training. These and further objects will become clear by reading the disclosure in conjunction with the drawings.

SUMMARY OF THE INVENTION

To reduce X-ray exposure while improving image quality, an area of interest is selected in the image. The image of the selected area is updated frequently, comparable to a rate of updates used today for the whole image. The rest of the image is updated at a significantly lower rate. Since the area of interest normally is a small part of the overall area, the total exposure is reduced significantly. A fast X-ray shutter, placed near the X-ray source, blocks the radiation from areas outside the area of interest. The shutter automatically retracts when the complete image is updated. The area of interest can be selected by the user or automatically selected based on activity in the image. Since most of the exposures are taken at a reduced collimation angle, limited by the area of interest, the area of interest is imaged at reduced scatter and better quality.

DETAILED DISCLOSURE

To reduce X-ray exposure while improving image quality, an area of interest is selected in the image. The image of the selected area is updated frequently, comparable to rate of updates used today for the whole image, typically 10-50 frames per second. The rest of the image is updated at a significantly lower rate, typically 1 to 4 frames per second. Since the area of interest normally is a small part of the overall area, the total exposure is reduced significantly.

Figure 1:
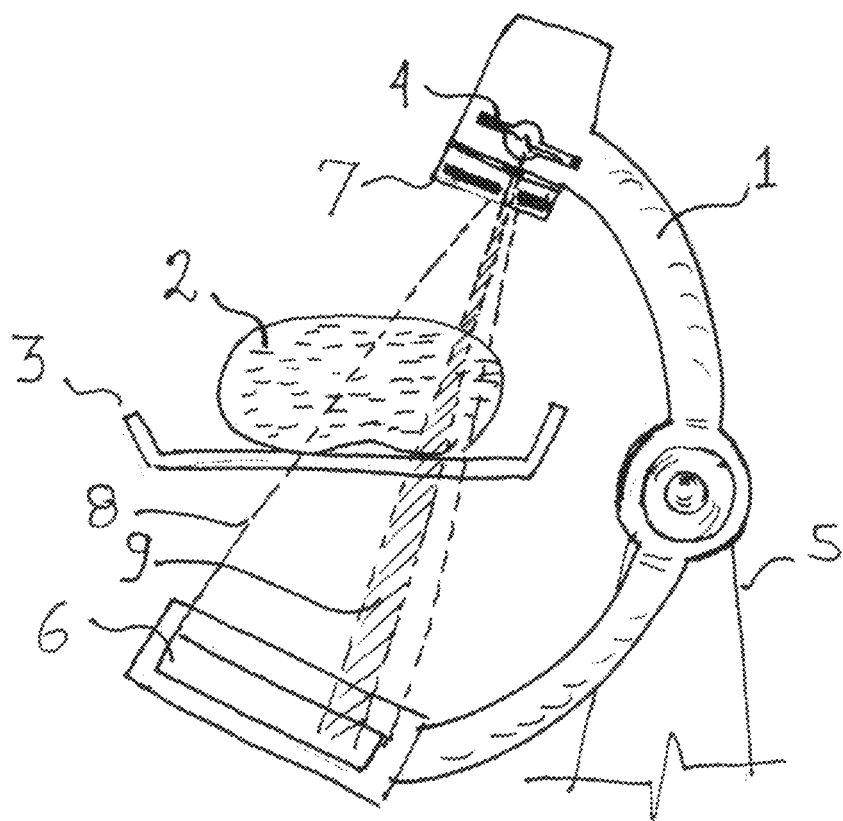
FIG. 1 shows a simplified view of a fluoroscopy system.

A typical X-ray fluoroscopy system is shown in FIG. 1. An arm 1 carries an X-ray source 4 at one end and a digital X-ray image sensor 6 at the other end. A patient 3 is supported on table 3 and placed between source 4 and sensor 6. Sensor 6 can be an analog sensor or a 2D solid state digital sensor panel. The system is typically mounted on a cart (not shown) via column 5 which allows positioning arm 1 in any position relative to patient 2. An automatic X-ray masking unit, or shutter, 7 is added near source 4. This masking unit is a fast operating shutter and it is used in addition to the standard masking unit, also known as a "collimator," which is built into most X-ray machines. The standard unit, even when motorized, is not capable of functioning as a fast shutter as it is intended to be adjusted manually once for a sequence of exposures. Masking unit 7 can automatically change the beam from a wide beam 8 to a narrow beam 9 directed at the area of interest. Since the radiation is mainly used in the form of narrow beam 9 and only used in the full width beam 8 to update the less important image parts, a significant reduction of radiation is achieved both for the patient and the doctor. It is known in the art of radiology that working with a narrow beam greatly improves image quality by reducing X-ray scatter reaching the detector. This is sometimes referred to as "coning down", i.e. reducing the X-ray cone angle. The system disclosed here operates most of the time in a minimal cone, greatly improving image quality in the area of interest. In this disclosure the terms X-ray and fluoroscopy are used interchangeably and the terms "mask", "shutter" and "shield-"should be broadly interpreted as anything that can interfere with the normal propagation of X-rays, not only by absorption but also by refraction, diffraction or any other interaction mechanism.

Figure 2:
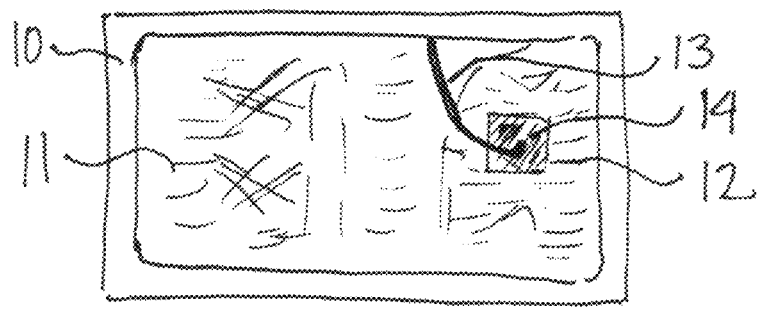
FIG. 2 shows the appearance of a fluoroscopy display according to the invention.

The reduction of radiation can be appreciated from FIG. 2. A screen 10 displays a real-time X-ray image 11. By the way of example, a tool such as guide-wire 13 is inserted into the body. The area of interest is at the tip 14 of the guide wire, since the rest of the wire is not free to move (e.g. it is usually confined to a blood vessel or other lumen). A small area of interest 12 is chosen and this area is updated at the full rate. The rest of the image 11 is updated at a significantly lower rate. By the way of example, if the area of interest is 10% in width and 10% in height of image 11 it occupies 1% of the area. If this 1% is updated at the full rate, for example 30 frames per second, while the rest of the image is updated at 1/30 of this rate (i.e. once per second), the total radiation will be 1%+1/30 of 100%=4.3% of the previously used dose. This represents a reduction of 23 fold. In practical terms this will allow the lead aprons to be significantly lighter and may eliminate the need for the lead glass goggles. The area of interest 14 can be manually selected by the user or can be automatically selected by a computer based on the activity in the image 11. Typically areas with very slow changes in image 11 are of little interest. Areas of interest, like the end of a guide wire or an angioplasty balloon, change rapidly as they are being manipulated by the doctor. By looking at the rate of change in the image the area of interest can be automatically selected. Sometimes there could be multiple areas of interest, requiring multiple windows 14 in one image. The higher radiation level area 14 is exposed to radiation comparable to the radiation density the whole area was exposed to in prior art systems. The areas outside the higher radiation area 14 are now exposed to a significantly lower radiation level.

Figure 4:
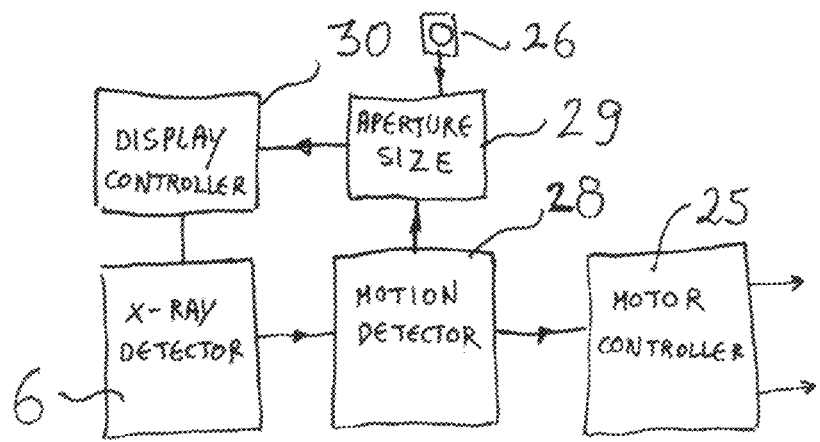
FIG. 4 is a block diagram of an automatic aperture selector.

A block diagram of such automatic selection based on activity is shown in FIG. 4. An X ray image sensor, or detector, 6 is connected to a display via a computer or display controller 30. A motion detector 28 determines the area of interest by monitoring the rate of change in the image. The algorithms for rate of change are well known in the art, and are typically based on subtracting consecutive frames. The larger the rate of change, the larger the difference between consecutive frames. An aperture size is selected by module 29, covering the area or areas where the rate of change exceeded a set threshold. This is fed to display controller 30 as well as to the controller 25 activating the variable masking mechanism which is explained later. A manual over-ride aperture control 26 can also be used to allow the user to change the dimensions of the selected aperture.

The variable aperture mask comprises X-ray shields mounted on actuators. X-ray shields are typically made of lead but any heavy metal and some non-metals can be used. When lead is used the thickness of the shield, or mask, is typically in the range of 0.2-10 mm.

The actuators control the shields to form an aperture. This aperture limits the radiation for most of the time. The actuators open up the aperture rapidly to expose the whole image for a small fraction of the time, typically from 1% to 10% of the time.

Figure 3:
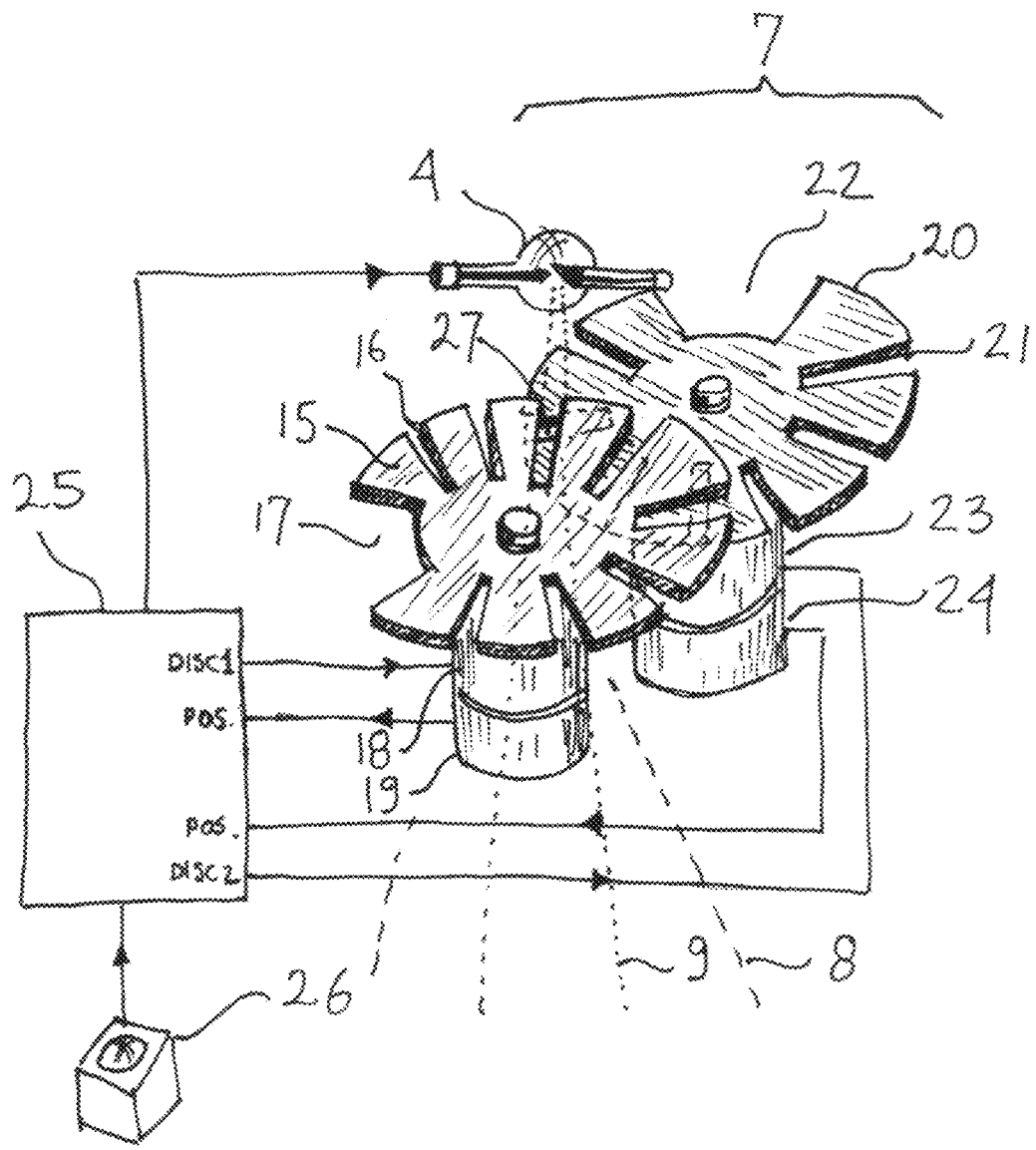
FIG. 3 is an isometric view of a rotary automatic masking unit.
Figure 5:
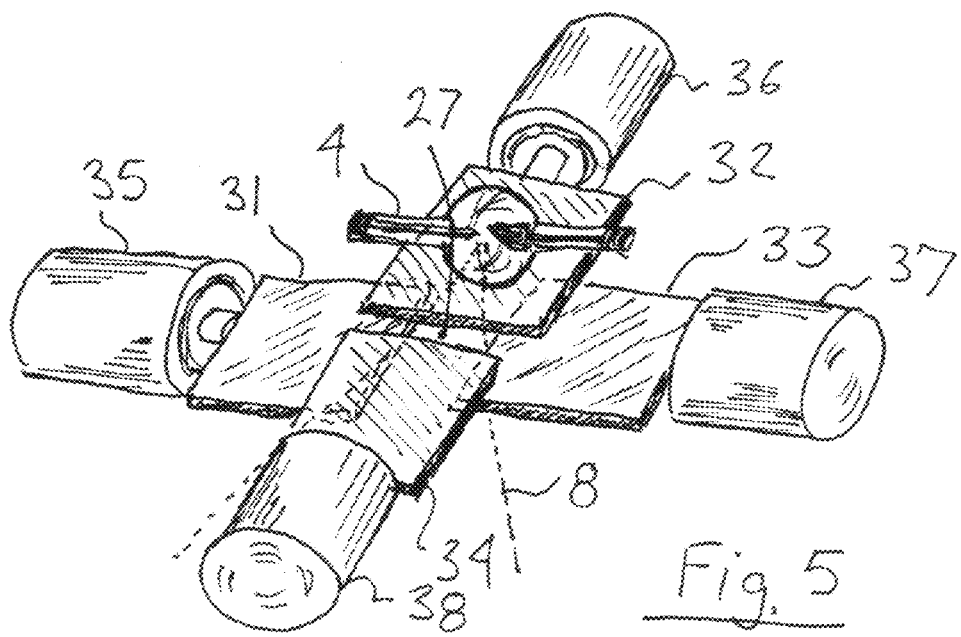
FIG. 5 is an isometric view of a linear automatic masking unit.
Figure 6:
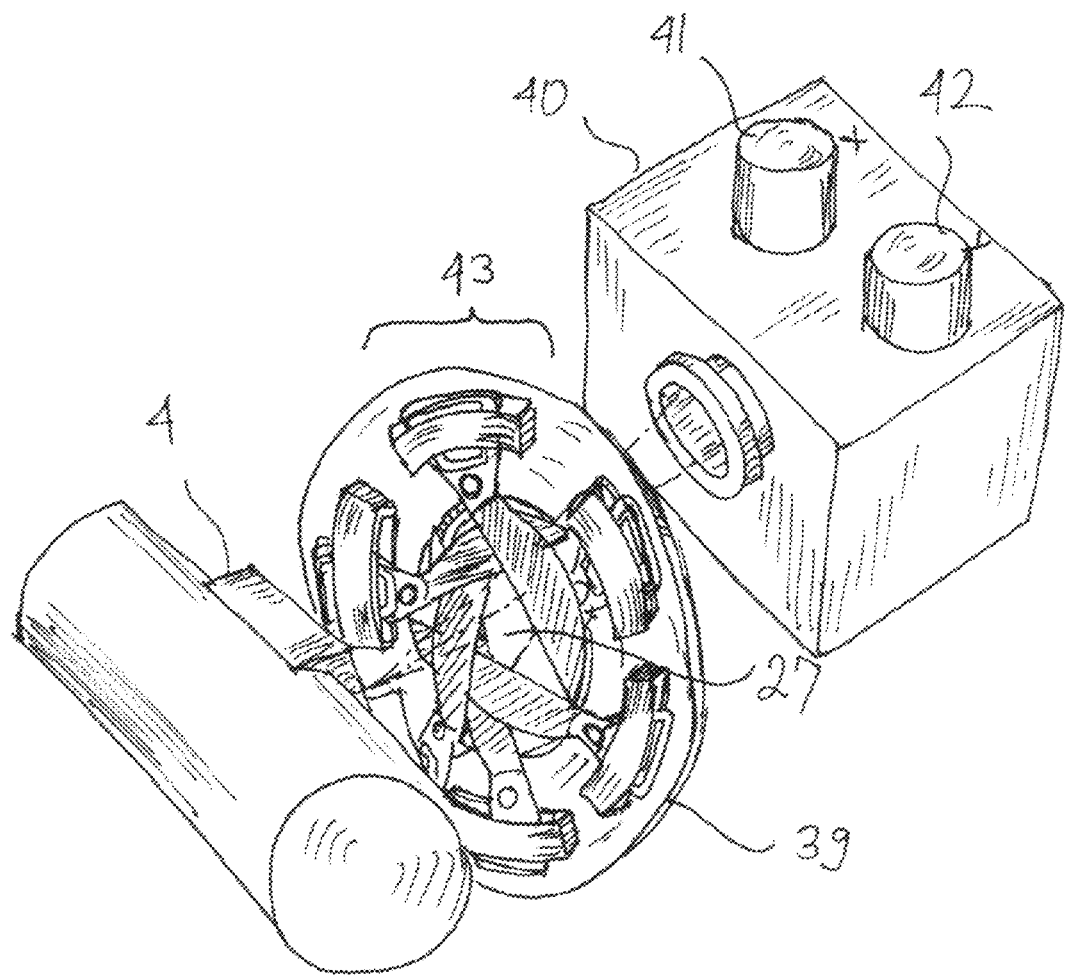
FIG. 6 is an exploded view showing the preferred placement of the shutter unit.
Figure 7:
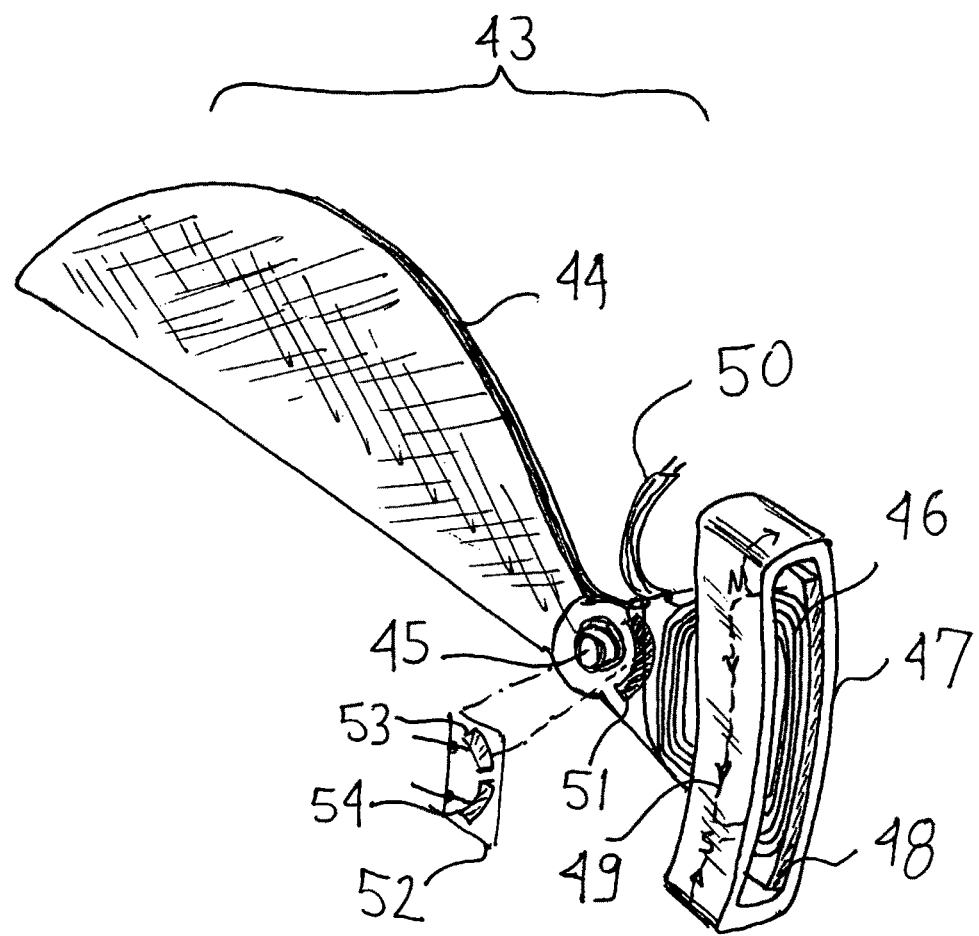
FIG. 7 is an isometric view of a single shutter blade actuator.

Three embodiments are disclosed, one based on rotary actuators is shown in FIG. 3 and one based on linear actuators is shown in FIG. 5. A third one, based on limited angle rotary actuators is shown in FIGS. 6 and 7.

Referring now to FIG. 3, a masking unit 7 comprises two rotary masks 15 and 20, typically made of lead sheet, rotated by two servo motors 18 and 23, having shaft encoders 19 and 24. A motor controller 25 controls the speed and relative position of the motors and triggers the activation of the X-ray source 4 whenever the masks are at the correct position. Each mask has a plurality of narrow slots 16 and 21 as well as at least one wide slot 17 and 22. When the wide slots 17 and 22 overlap the full image is exposed by a wide beam 8. When the narrow slots overlap a small aperture 27 is formed, allowing only a narrow beam 9 to expose the patient and update the area of interest in the image. The relative position of aperture 27 in the image is controlled by advancing or retarding the position of one motor relative to the other. For example, if the position of mask 15 will be advanced clockwise relative to mask 20, aperture 27 will move to the right. Similarly, if the position of mask 20 will be advanced clockwise, aperture 27 will move up. Masks 15 and 20 can be continuously rotated or stepped by stepper motors. Masks 15 and 20 can be slaved to the firing rate of X-ray source 4 or the firing of source 4 can be slaved to the position of the masks. For highest speed operation (i.e. the highest rate of frames per second) it is best to have the masks rotate continuously and slave the firing of the source to the position of the masks. The system of FIG. 3 allows positioning of the aperture 27 anywhere in the image but does not allow changing the aperture size. By replacing each mask wheel by two parallel wheels, each having its own motor, the size of the mask can be controlled by the relative position of the mask wheels, as the mask will be the overlap of the two slots in each direction. An alternate embodiment has only two wheels, as shown in FIG. 3, but each wheel has multiple sets of slots, each set of a different width. This allows selecting the aperture width and aperture height independently in discrete steps. The desired aperture position and size can be selected automatically or manually, by using an interface device such a trackball 26 or any other pointing device such as a computer mouse, joystick, touch screen etc.

A linear masking embodiment is shown in FIG. 5. Masking shields 31, 32, 33 and 34 are moved by linear actuators 35, 36, 37 and 38. The opening between the masks forms the aperture 27. The operation is similar to the rotary mask. Both the position and size of aperture 27 are easily variable. Most of the time aperture 27 is small, periodically opening for a full exposure. Actuators 35-38 can be of the moving coil type, commercially available from companies such as Kimco (www.beikimco.com/actuators_linear.php). They can incorporate linear encoders (not shown) when operated in close-loop mode. Linear masking is typically more versatile than rotary masking but slower (for a given size and input power).

It is desirable to place the masking unit, or shutter, close to the X-ray source in order to minimize the mass of the shutter blades. A design of a masking unit having minimal thickness is shown in FIG. 6. This design is based on current computer disc drive technology and can be made very thin (about 10 mm). This allows placing the unit between the X-ray tube and the standard built-in collimator. At that point the beam size in most X-ray machines is less than 40 mm and a very small and fast shutter can be used. Referring now to FIG. 6, a masking unit 39 comprising multiple actuators 43, each one carrying an X-ray blocking blade, is placed between X-ray tube 4 and standard masking unit (collimator) 40. In FIG. 6 a six actuator configuration is shown, to reduce the mass of each shutter blade, but any number of actuators can be used. The standard masking unit 40, which is not part of the disclosure, is typically controlled by electric motors 41 and 42 to adjust X and Y collimation plus a rotation adjustment (not shown). The aperture 27 can be placed anywhere within the beam and the size of aperture 27 can be adjusted over a wide range by individually moving actuators 43. The firing of the X-ray source can be synchronized to shutter position or vice versa.

The construction of a single actuator unit 43 is shown in FIG. 7. It is based on the well known data storage disc actuator. These actuators can be made very thin, as evident by disc drives less than 10 mm in thickness. Shutter blade 44 is attached to moving coil 46 and is mounted for pivoting around shaft 45, typically by using a pair of ball bearings. Shutter blade 44 can be made of lead but for higher performance it is better to use a sheet of lead clad with, or laminated between, sheets of steel. This creates a rigid and strong X-ray shield. Typical thickness would be 1 mm lead clad between two sheets of 0.25 mm steel. A flat rare earth magnet 48 generates magnetic field 49 in a mild steel frame 47. Since the field penetrates the air gap in one direction at the top of the actuator and in the opposite direction at the bottom, the forces from both sides of the coil add up. Since this type of actuator can be found in any computer disc drive it is well understood and will not be detailed further. The connections to the moving coil (and sensors, if needed) are made via a flexible printed circuit board 50. In order to measure the shutter blade position any angular encoder can be used, such as a differential capacitive encoder. Assume electrode 51 is grounded and electrodes 53 and 54 of capacitive sensor 52 are placed in proximity to electrode 51. As the moving coil 46 turns clockwise, the capacitance to ground of electrode 54 increases and that of electrode 53 decreases. The capacitance ratio between electrodes 54 and 53 is proportional to the rotation angle. The art of angular transducers is well known and needs no further detailing. The sensing can also be performed by optical or electromagnetic encoders. For higher accuracy an Inductosyn ™ type electromagnetic encoder can be used.

As mentioned earlier, the disclosed method will increase the image quality inside the area of interest while reducing the radiation because X-ray scattering will be greatly reduced during the majority of the exposures, since they are done with a narrow beam. The image quality outside the area of interest will remain the same as a conventional image. The refresh rate outside the area of interest can be chosen by the user, typically in the range of several exposures per second, or can be selected automatically based on the rate of change in the image, as explained later.

Figure 8A:
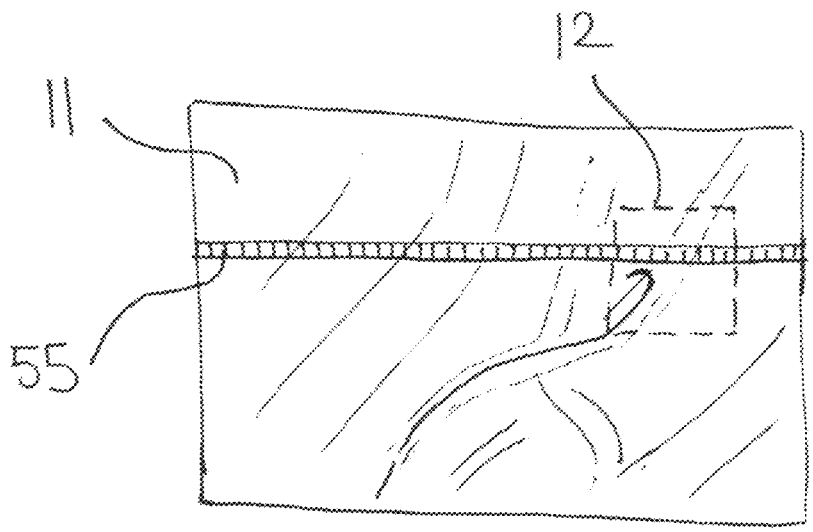
FIG. 8 shows schematically a method of combining the image of the area of interest with the rest of the image.
Figure 8B:
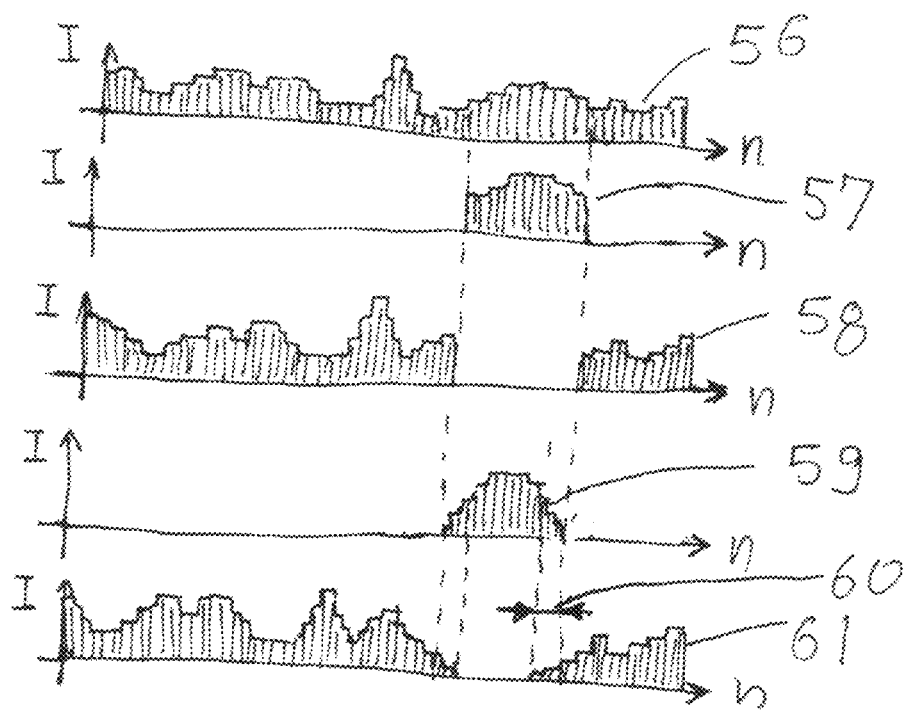

FIGS. 8A and 8B show how the area of interest image 12 is inserted into the background image 11. A single image line 55 is shown in FIG. 8B. The vertical axis is the intensity and the horizontal axis is the pixel number n. A line from the background image is shown by 56 and a line from the area-of-interest image is shown by 57. Clearly the majority of the images in a sequence will only include the area of interest. One of the simplest algorithms to combine, or "fuse", the images is to subtract the first area-of-interest image (line 57) from the background image (line 56) to create a mask (line 58). This mask is updated each time the shutter opens fully and a new background image is created. Such a simple algorithm may create a visible artifact at the border between the two images, partly because of the higher image quality (lower scatter noise) of the inserted image. Such a border may actually be desirable, to denote the higher resolution area, and may be emphasized by an added line. If a boundary is not desirable, more advanced image merging algorithms similar to the ones used in fusing photographs can be used. One such algorithm creates an overlap area 60 between the inserted image 59 and background image 61. In the overlap area the pixels of the inserted image are assigned an increasing weight as the image border moves towards the inserted image. By the way of example, if the overlap area is 10 pixels wide, the first pixel is calculated as 90% of the value of the background plus 10% of the value of the inserted (i.e. area of interest) image. The second pixel is 80% of the background pixel value plus 20% of the inserted image pixel value, the third is 70%+30% and so on. In order to match the noise appearance between the images noise dithering or noise addition techniques can be used.

When the majority of the image is not changing or changing slowly, and the area-of-interest is the only area with rapid changes, the determination of the area-of-interest is simple and can be done by simply subtracting images. In many situations, such as cardiology, there are also rapid changes in the background such as a beating heart. In spite of the rapid changes it is still possible to separate the area of interest from the background if the background changes are periodic, as in the example of a beating heart.

There are several ways of achieving that:

1. Taking a sequence of images at high refresh rate to determine what motions are periodic and which are non-periodic and therefore should be in the area of interest.

2. Synchronizing the pulsed X-ray source to an EKG signal (or any other signal related to the periodic motion such as blood pressure) when the background image is taken. This will cause all areas of periodic motion to appear motionless and be placed outside the area of interest. This method is of particular interest in cardiology since the heart rate, EKG and blood pressure signals are normally monitored during the procedure and any one of them can be used.

3. Typically inserted devices such as catheters, probes or guide-wires have well defined geometric shapes such as being elongated and having sharp edges. The software can identify such shapes, or a "teach mode" can be used in which the user places an initial window around such a shape from which the software learns it and can track it.

4. Any combination of the above strategies. Such a medical device, inserted into the body, can be considered an "object of interest" and be tracked by the software.

In general the area of interest can be selected based on the contents of the image (features, motion etc) or based on a different criteria such as manual input (using a touch screen, mouse, pointing device etc). Once an area-of-interest is selected the software can also calculate and record the actual radiation the patient received based on the full image radiation and the respective time spent at different collimations. Such radiation monitoring and recording is becoming increasingly important as the use of X-ray increases.

Figure 9:
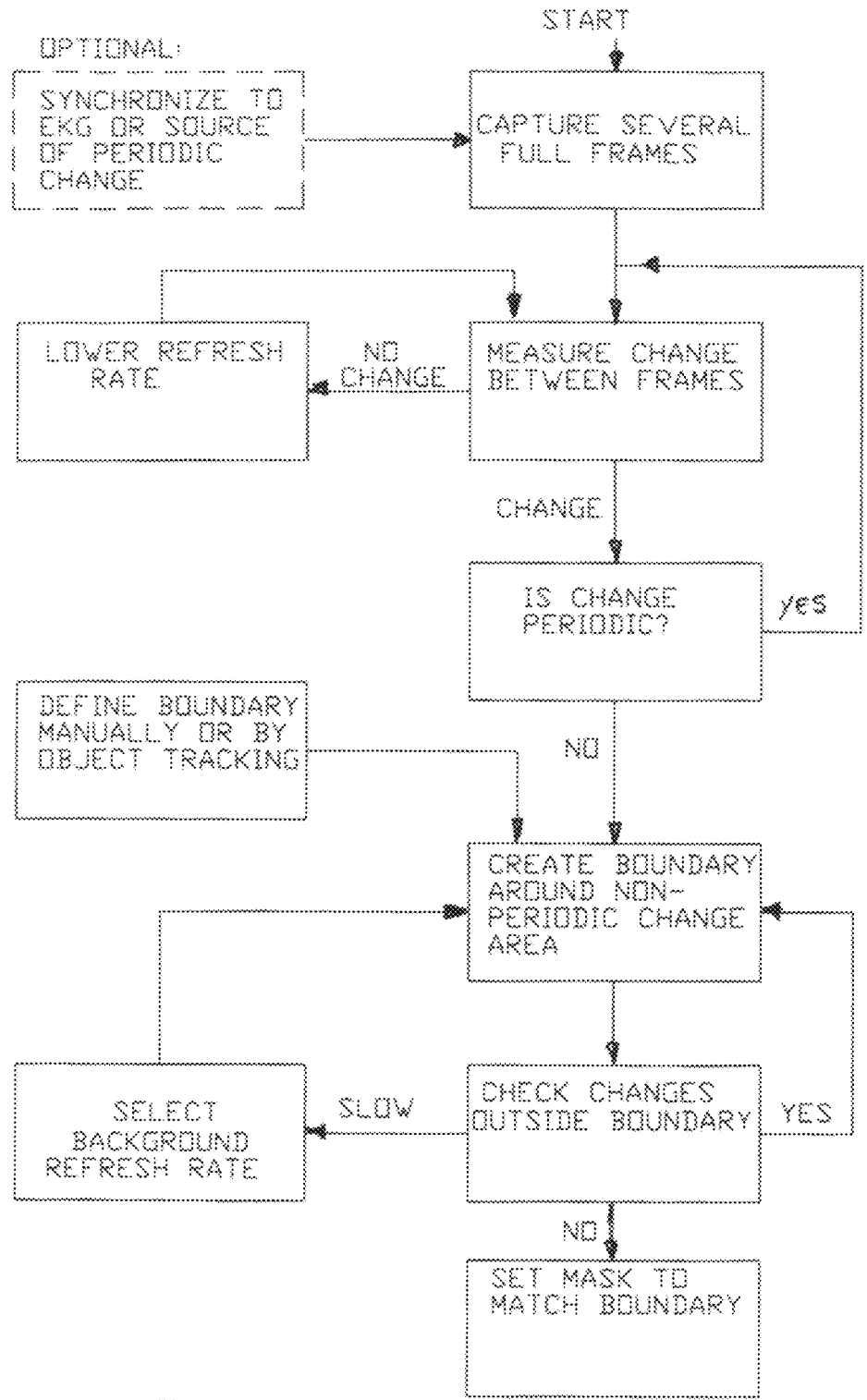
FIG. 9 is a flow chart of an algorithm defining an area of interest.

A sample flow chart for determining the area-of-interest and varying it during the procedure is shown in FIG. 9. Clearly this is just one of many possible algorithms, but in general all would start with a full frame image or sequence of imaging. From this an area of interest is selected either manually or automatically. The background image (area outside the area-of-interest) is checked each time it is refreshed for changes. The more changes found the higher the background refresh rate is selected. If changes appear significant or above a pre-set selectable threshold the area of interest is expanded to include the changing areas. It should be pointed out that changing the refresh rate for the full image based on the rate of change in the image is not a new idea, the novelty is, among other things, in refreshing part of the image at a different rate than other parts and imaging the area of interest with a better quality, because of the smaller X-ray come, than the rest of the image.

In some cases the area of interest will be selected not because of rate-of-change but because the geometric shape. For example, when a cardiologist is trying to break through a total coronary occlusion there may not be much motion but the area of interest is limited to the tip of the tool. This can be defined by the user or selected by recognizing the unique geometric features of the tool as explained earlier. Methods for identifying a position of a tool are well known in image analysis and disclosed in U.S. patent publication 2008/0118115 hereby incorporated herein by reference.

The invention claimed is:

1. An X-ray imaging system for displaying an image on a monitor, said system comprising an X-ray source, a collimator, and a masking unit comprising an adjustable shutter located between the X-ray source and the collimator, wherein the masking unit is configured to control the shutter so that part of said image is created at a higher refresh rate using a narrower X-ray beam than the rest of said image, said narrower beam defined by the shutter.

2. A system as in claim 1 wherein said masking unit comprises a plurality of moving coil rotary actuators connected to operate X-ray blocking blades of the shutter.

3. A system as in claim 1 wherein said image part created at the higher refresh rates and the rest of said image created at a lower refresh rate are blended seamlessly by using an image overlap region.

4. A system as in claim 1 wherein the firing of the X-ray source is synchronized to the position of said shutter.

5. A method for improving the resolution of a sequence of X-ray images while reducing the radiation level used, said method comprising the steps of:
  selecting an area-of-interest in said images;
  exposing said area-of interest at first refresh rate using a cone of X-rays matched to a size of said area-of-interest; and
  exposing full images with an X-ray cone covering the full images at a second refresh rate slower than said first refresh rate.

6. A method as in claim 5 wherein the area-of-interest is automatically selected by the system based on rates of change in the images.

7. A method as in claim 5 wherein the area-of-interest is defined automatically based on the change from image to image.

8. A method as in claim 5 wherein the area-of-interest is defined automatically based on the change from image to image, said change excluding periodic change.

9. A method as in claim 5 wherein the area-of-interest is defined automatically based on image to image, said changes excluding periodic changes by synchronizing operation of an X-ray source used to generate said images to a signal derived from said periodic changes.

10. A method as in claim 5 wherein said full image and said area-of-interest are blended seamlessly by using an image overlap region between both images.

11. A method as in claim 5 wherein said full image and said area-of-interest are blended seamlessly by using an image overlap region between both images and the pixel values in the area of interest are affected by both images.

12. A method as in claim 5 wherein both the location and shape of the area-of-interest can be selected by the user.

13. A method as in claim 5 wherein both the location and shape of the area-of-interest are selected automatically.

14. A method as in claim 5 wherein both the location and shape of the area-of-interest can be selected automatically by recognizing features of an object of interest.

15. A method as in claim 5 wherein the refresh rate outside the area-of-interest is automatically selected based on the detected rate of change of the images.

16. A method as in claim 5 wherein the area-of-interest is one of a plurality of areas-of-interest and the method comprises exposing each of said areas-of-interest to a radiation level higher than a radiation level delivered within said images outside of said areas-of-interest.

17. A method according to claim 5 wherein exposing said area-of-interest comprises delivering pulses from a pulsed X-ray source.

18. A method according to claim 17 comprising slaving firing of the pulsed X-ray source to positions of masks that match the cone of X-rays to the size of said area-of-interest.

19. A method according to claim 18 comprising moving the masks continuously.

20. A method according to claim 19 wherein the masks comprise slotted rotary masks and the method comprises adjusting a position of the area-of-interest by advancing or retarding rotation of one of the masks relative to another one of the masks.

* * * * *